(12) United States Patent
Baril et al.

(10) Patent No.: US 11,944,367 B2
(45) Date of Patent: Apr. 2, 2024

(54) ELECTROSURGICAL DEVICE FOR CUTTING TISSUE

(71) Applicant: Covidien LP, Mansfield, MA (US)

(72) Inventors: Jacob C. Baril, Norwalk, CT (US); Matthew A. Dinino, Newington, CT (US); Justin Thomas, New Haven, CT (US); Roy J. Pilletere, North Haven, CT (US); Saumya Banerjee, Hamden, CT (US); Thomas A Zammataro, North Haven, CT (US); Scott J. Prior, Shelton, CT (US); Brian J. Creston, Shelton, CT (US)

(73) Assignee: Covidien LP, Mansfield, MA (US)

( * ) Notice: Subject to any disclaimer, the term of this patent is extended or adjusted under 35 U.S.C. 154(b) by 1056 days.

(21) Appl. No.: 16/782,601

(22) Filed: Feb. 5, 2020

(65) Prior Publication Data

US 2021/0236188 A1  Aug. 5, 2021

(51) Int. Cl.
*A61B 18/08* (2006.01)
*A61B 18/00* (2006.01)
*A61B 18/16* (2006.01)

(52) U.S. Cl.
CPC .... *A61B 18/08* (2013.01); *A61B 2018/00083* (2013.01); *A61B 2018/00178* (2013.01); *A61B 2018/00202* (2013.01); *A61B 2018/00607* (2013.01); *A61B 18/16* (2013.01); *A61B 2018/162* (2013.01)

(58) Field of Classification Search
CPC ........... A61B 2018/00083; A61B 2018/00178; A61B 2018/00202; A61B 2018/00601; A61B 2018/00607; A61B 2018/1465; A61B 2018/1475; A61B 18/16; A61B 2018/162
See application file for complete search history.

(56) References Cited

U.S. PATENT DOCUMENTS

| | | | |
|---|---|---|---|
| 2,022,065 A | 11/1935 | Wappler | |
| 2,047,535 A | 7/1936 | Wappler | |
| 3,516,412 A | 6/1970 | Ackerman | |
| 3,886,944 A | 6/1975 | Jamshidi | |

(Continued)

FOREIGN PATENT DOCUMENTS

WO   2016025132 A1   2/2016

OTHER PUBLICATIONS

U.S. Appl. No. 16/540,593 to Baril et al.

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

A tool assembly for use with an electrosurgical device for cutting tissue includes a base portion, an electrical insulator extending distally from the base portion, a return lead adapted to be electrically coupled to a return terminal, and an active lead adapted to be electrically coupled to an active terminal. The return lead is movably supported on the electrical insulator. The active lead is fixed to the electrical insulator. The return lead is rotatable about a pivot and translatable along a longitudinal axis relative to the electrical insulator and the active lead. Upon activation, electrosurgical energy is transmitted from the active lead through tissue to the return lead to cut tissue in contact with the active lead.

20 Claims, 5 Drawing Sheets

(56) References Cited

U.S. PATENT DOCUMENTS

| | | |
|---|---|---|
| 4,161,950 A | 7/1979 | Doss et al. |
| 4,196,734 A | 4/1980 | Harris |
| 4,198,957 A | 4/1980 | Cage et al. |
| 4,485,810 A | 12/1984 | Beard |
| 4,534,347 A | 8/1985 | Taylor |
| 4,622,966 A | 11/1986 | Beard |
| 4,633,880 A | 1/1987 | Osypka et al. |
| 4,862,890 A | 9/1989 | Stasz et al. |
| 5,013,312 A | 5/1991 | Parins et al. |
| 5,047,027 A * | 9/1991 | Rydell ............... A61B 18/1482 606/50 |
| 5,085,659 A | 2/1992 | Rydell |
| 5,300,068 A | 4/1994 | Rosar et al. |
| 5,360,428 A | 11/1994 | Hutchinson, Jr. |
| 5,441,499 A | 8/1995 | Fritzsch |
| 5,484,435 A * | 1/1996 | Fleenor ............. A61B 18/1442 606/50 |
| 5,507,743 A * | 4/1996 | Edwards ........... A61B 18/1815 600/373 |
| 5,531,744 A | 7/1996 | Nardella et al. |
| 5,536,267 A | 7/1996 | Edwards et al. |
| 5,578,048 A | 11/1996 | Pasqualucci et al. |
| 5,599,295 A | 2/1997 | Rosen et al. |
| 5,599,346 A | 2/1997 | Edwards et al. |
| 5,611,798 A | 3/1997 | Eggers |
| 5,647,372 A | 7/1997 | Tovey et al. |
| 5,766,167 A | 6/1998 | Eggers et al. |
| 6,027,501 A | 2/2000 | Goble et al. |
| 6,217,528 B1 | 4/2001 | Koblish et al. |
| 6,494,881 B1 * | 12/2002 | Bales ................. A61B 18/149 606/49 |
| 6,530,924 B1 | 3/2003 | Ellman et al. |
| 6,533,781 B2 | 3/2003 | Heim et al. |
| 6,752,767 B2 | 6/2004 | Turovskiy et al. |
| 7,033,354 B2 | 4/2006 | Keppel |
| 7,156,844 B2 | 1/2007 | Reschke et al. |
| 7,371,234 B2 | 5/2008 | Young |
| 7,399,299 B2 | 7/2008 | Daniel et al. |
| 7,419,488 B2 | 9/2008 | Ciarrocca et al. |
| 7,846,108 B2 | 12/2010 | Turovskiy et al. |
| 7,846,158 B2 | 12/2010 | Podhajsky |
| 8,137,345 B2 | 3/2012 | McNall, III et al. |
| 8,734,464 B2 | 5/2014 | Grover et al. |
| 8,777,961 B2 | 7/2014 | Cabrera et al. |
| 8,968,301 B2 | 3/2015 | Weber |
| 8,968,329 B2 | 3/2015 | Cabrera |
| 9,060,765 B2 | 6/2015 | Rencher et al. |
| 9,358,065 B2 | 6/2016 | Ladtkow et al. |
| 9,445,863 B2 | 9/2016 | Batchelor et al. |
| 9,549,747 B2 | 1/2017 | Carlson |
| 9,592,067 B2 | 3/2017 | Hartoumbekis |
| 9,775,665 B2 | 10/2017 | Ellman |
| 9,987,031 B2 | 6/2018 | Menn |
| 9,993,229 B2 | 6/2018 | Whitfield |
| 9,993,287 B2 | 6/2018 | Sartor et al. |
| 10,034,661 B2 | 7/2018 | Holsten et al. |
| 10,045,761 B2 | 8/2018 | Weber |
| 10,154,833 B2 | 12/2018 | Holsten et al. |
| 10,376,314 B2 | 8/2019 | van der Weide et al. |
| 10,433,898 B2 | 10/2019 | Borgmeier et al. |
| 10,433,899 B2 | 10/2019 | Borgmeier et al. |
| 10,531,917 B2 | 1/2020 | Johnson et al. |
| 2001/0037055 A1 * | 11/2001 | Khatchatrian ..... A61B 10/0045 600/215 |
| 2005/0070895 A1 | 3/2005 | Ryan et al. |
| 2005/0283149 A1 | 12/2005 | Thorne et al. |
| 2007/0054539 A1 * | 3/2007 | Wakikaido ......... A61B 18/1442 439/402 |
| 2007/0078454 A1 | 4/2007 | McPherson |
| 2007/0118110 A1 | 5/2007 | Girard et al. |
| 2007/0149966 A1 | 6/2007 | Dahla et al. |
| 2007/0149971 A1 * | 6/2007 | Nishimura ......... A61B 18/1445 606/51 |
| 2007/0179494 A1 | 8/2007 | Faure |
| 2007/0219546 A1 | 9/2007 | Mody et al. |
| 2007/0260240 A1 | 11/2007 | Rusin |
| 2007/0265609 A1 | 11/2007 | Thapliyal et al. |
| 2008/0281323 A1 | 11/2008 | Burbank et al. |
| 2009/0306642 A1 | 12/2009 | Vankov |
| 2012/0095454 A1 * | 4/2012 | Cox ................... A61B 18/1402 606/41 |
| 2012/0116416 A1 | 5/2012 | Neff et al. |
| 2013/0255063 A1 | 10/2013 | Hart et al. |
| 2013/0267947 A1 | 10/2013 | Orszulak |
| 2014/0236143 A1 * | 8/2014 | Ward ................. A61B 18/1442 606/39 |
| 2018/0206903 A1 * | 7/2018 | Podany ............. A61B 18/1442 |
| 2019/0083172 A1 | 3/2019 | Ladtkow et al. |
| 2019/0321018 A1 | 10/2019 | Prior |

* cited by examiner

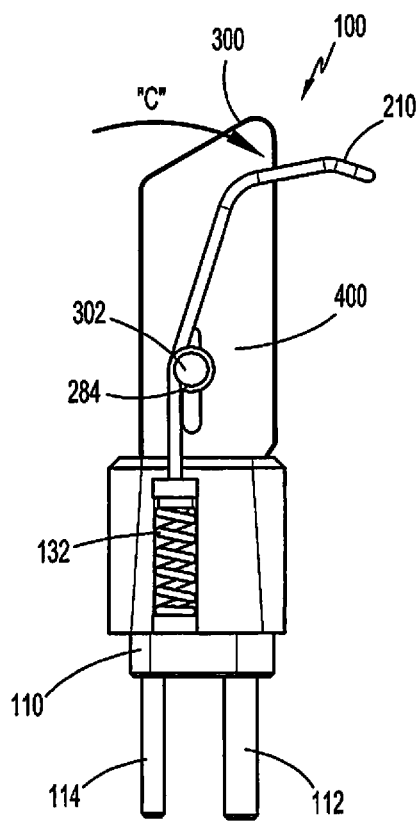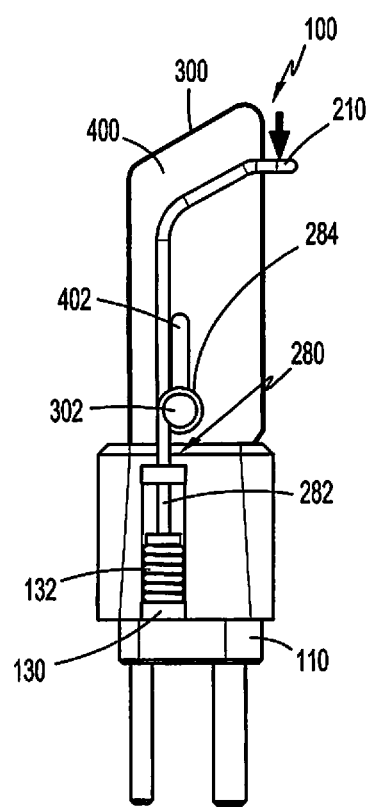
FIG. 2  FIG. 3
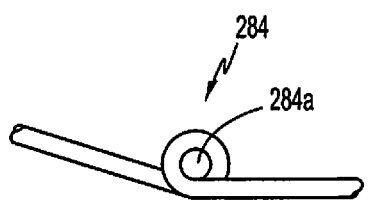
FIG. 4A
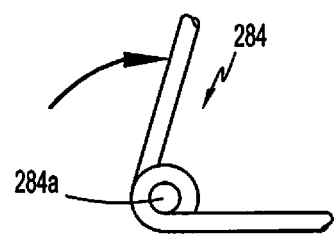
FIG. 4B

ELECTROSURGICAL DEVICE FOR CUTTING TISSUE

FIELD

The present disclosure relates to surgical devices and, more particularly, to bipolar electrosurgical devices for cutting tissue.

BACKGROUND

Laparoscopic surgery is increasingly common. The principle of laparoscopic surgery is to perform a surgical procedure with small keyhole incisions. Usually, two or three such keyhole incisions are made in the abdomen for insertion of a telescopic video camera, laparoscopic instruments, and/or electrosurgical devices. Electrosurgical devices are used in both open and laparoscopic surgical procedures to cut and/or coagulate tissue. Various types of electrosurgical devices are known, including those that use diathermy with either monopolar or bipolar current, and advanced devices such as harmonic scissors and argon beam and laser devices. Monopolar and bipolar devices use one or two electrodes, respectively, to deliver electrical energy from a current source to the surgical site. By varying the voltage, current, or waveform of the electrical energy delivered by the electrode(s), surgeons can cut tissue, coagulate tissue to stop bleeding, or produce a "blended cut" that combines these two functions.

SUMMARY

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In accordance with an aspect of the present disclosure, a tool assembly for use with an electrosurgical device for cutting tissue includes a base portion, an electrical insulator extending distally from the base portion, a return lead adapted to be electrically coupled to a return terminal, and an active lead adapted to be electrically coupled to an active terminal. The return lead is movably supported on the electrical insulator. The active lead is fixed to the electrical insulator. The return lead is rotatable about a pivot and translatable along a longitudinal axis relative to the electrical insulator and the active lead. Upon activation, electrosurgical energy is transmitted from the active lead through tissue to the return lead to cut tissue in contact with the active lead.

In an aspect of the present disclosure, the active lead may be fixed to a peripheral portion of the electrical insulator that may define an acute angle with the longitudinal axis.

In another aspect of the present disclosure, the return lead may include a neck portion extending along the longitudinal axis, and an engaging portion offset from the longitudinal axis.

In yet another aspect of the present disclosure, the engaging portion of the return lead may be rotatable about a pivot on the neck portion of the return lead.

In still another aspect of the present disclosure, the engaging portion of the return lead may be rotatable between a first position, in which, the engaging portion is parallel to the peripheral portion of the electrical insulator, and a second position, in which, the engaging portion defines an acute angle with the peripheral portion of the electrical insulator.

In still yet another aspect of the present disclosure, the tool assembly may further include a torsion spring configured to bias the engaging portion of the return lead to the first position.

In another aspect of the present disclosure, the electrical insulator may define a slot along a length thereof. The slot may be configured to receive a camming pin extending through an opening of the torsion spring.

In yet another aspect of the present disclosure, the base portion may include an axial member operatively coupled with the camming pin, and a compression spring configured to bias the axial member towards a distal-most position.

In still yet another aspect of the present disclosure, the compression spring may be disposed along the longitudinal axis.

In still yet another aspect of the present disclosure, the electrical insulator may be formed of ceramic.

In still yet another aspect of the present disclosure, the return lead may be formed of stainless steel.

In still yet another aspect of the present disclosure, the active lead may be formed of tungsten.

In still yet another aspect of the present disclosure, a portion of the engaging portion of the return lead may be dimensioned to be laterally outward of a lateral portion of the electrical insulator.

In accordance with another aspect of the present disclosure, a tool assembly for use with an electrosurgical device for cutting tissue includes a base portion defining first and second bores, an electrical insulator received through the first bore of the base portion, an active lead adapted to be electrically coupled to a first electrical potential, and a return lead adapted to be electrically coupled to a second electrical potential and positioned relative to the active lead to define a gap therebetween. A portion of the active lead is disposed in the electrical insulator. The active lead includes a needle portion extending distally from the base portion. The return lead includes an extension portion extending distally from the base portion and an engaging portion extending laterally outward from the extension portion. Upon activation, electrosurgical energy is transmitted between the first and second electrical potentials and through tissue disposed therebetween.

In an aspect of the present disclosure, the engaging portion and the extension portion of the return lead may be orthogonal to each other such that the engaging portion extends away from the active lead.

In another aspect of the present disclosure, at least the needle portion of the active lead may be formed of tungsten.

In still another aspect of the present disclosure, the electrical insulator may be formed of ceramic.

In accordance with another aspect of the present disclosure, a tool assembly for use with an electrosurgical device for cutting tissue includes a base portion, an electrical insulator extending through the base portion, an active lead adapted to be electrically coupled to a first electrical potential, and a return lead adapted to be electrically coupled to a second electrical potential. A portion of the active lead is disposed in the electrical insulator. The active lead includes a blade portion defining a first plane. The return lead extends through the base portion. The return lead is positioned relative to the active lead to define a gap therebetween. The return lead defines a second plane orthogonal to the first plane of the active lead. Upon activation, electrosurgical energy is transmitted between the first and second electrical potentials and through tissue disposed therebetween.

In an aspect of the present disclosure, the active lead may be formed of tungsten.

In another aspect of the present disclosure, at least one of the active lead or the return lead may have a flat profile.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIG. 2 is a side cross-sectional view of the tool assembly of FIG. 1A, illustrating rotation of a return lead;

FIG. 3 is a side cross-sectional view of the tool assembly of FIG. 1A, illustrating axial displacement of the return lead;

FIGS. 4A and 4B are side views of a torsion spring of the tool assembly of FIG. 1A, illustrating use thereof;

DETAILED DESCRIPTION

Figure 1A:
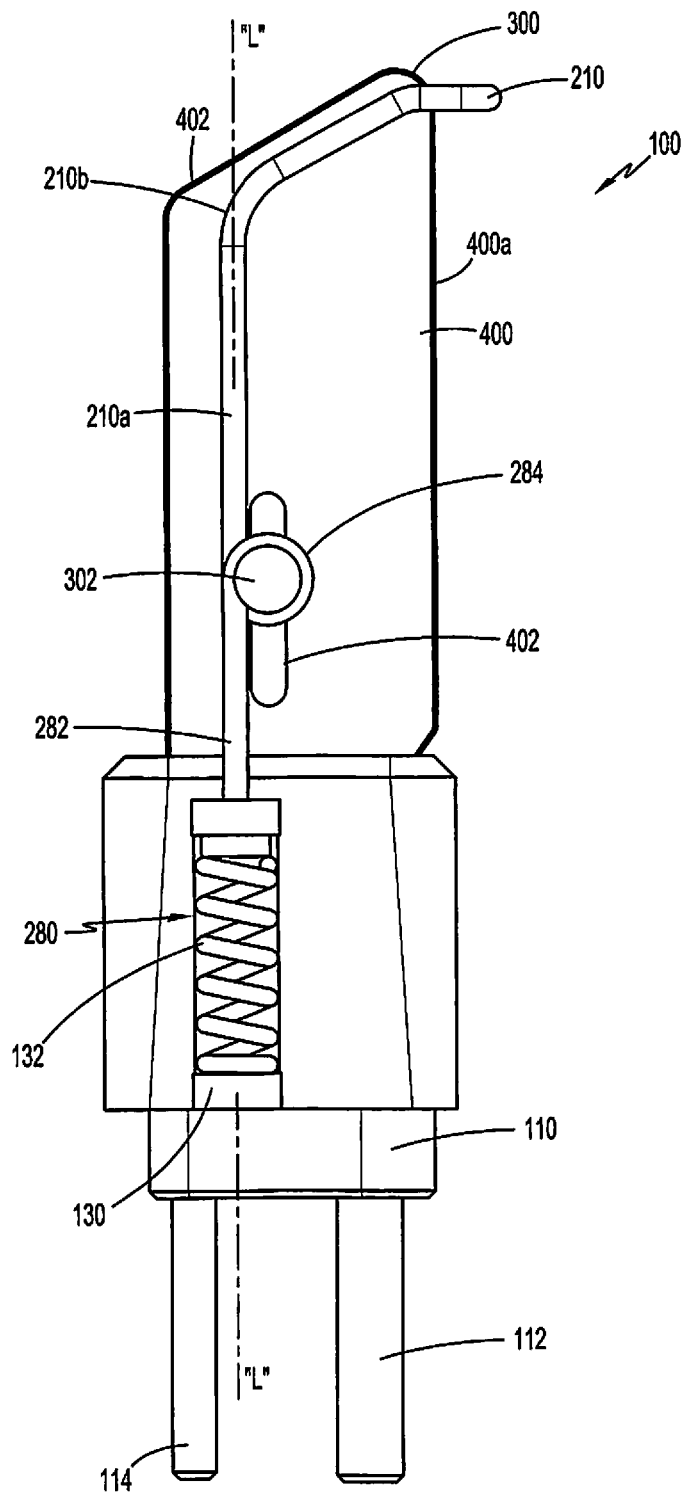
FIG. 1A is a side cross-sectional view of a tool assembly for use with an electrosurgical device in accordance with an aspect of the present disclosure.
Figure 1B:
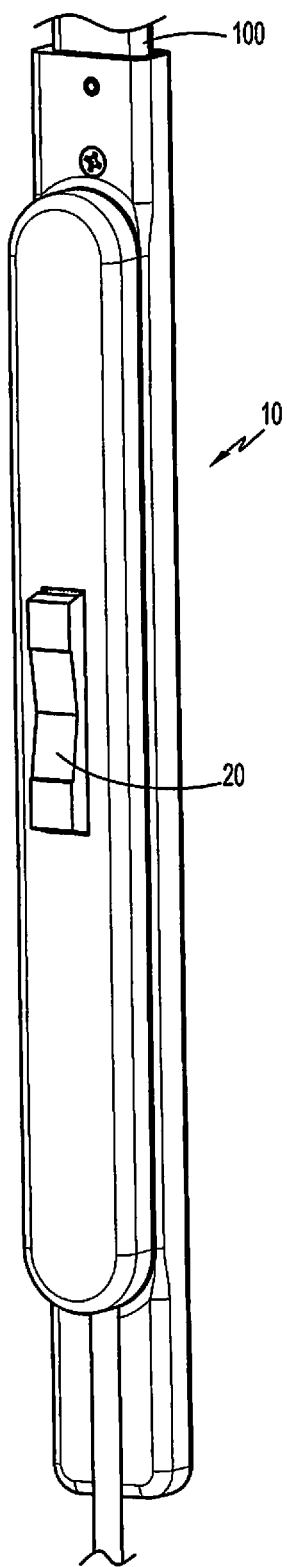
FIG. 1B is a perspective view of a handle of the electrosurgical device for use with the tool assembly of FIG. 1A.
Figure 5:
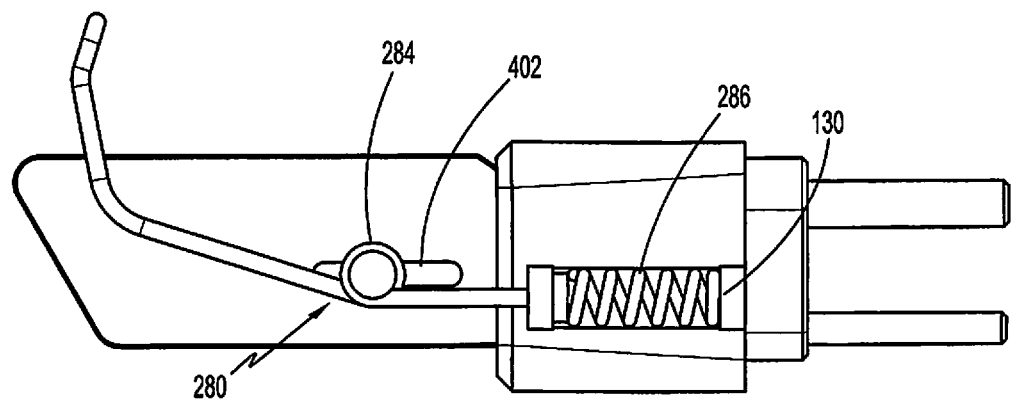
FIG. 5 is a side cross-sectional view of an actuation assembly of the return lead of the tool assembly of FIG. 1A.

Turning now to FIG. 1A, a tool assembly for use with an electrosurgical device in accordance with an aspect of the present disclosure is generally shown as a tool assembly 100 adapted to be electrically coupled to an electrosurgical energy source such as, e.g., a generator (not shown), to provide bipolar radio-frequency (RF) power output. The electrosurgical energy source may include electronic circuitry configured to generate radio frequency energy specifically suited for various electrosurgical modes and/or procedures. The electrosurgical energy source may include one or more converting devices for converting from DC to AC or vice versa. The electrosurgical device may be configured to transmit any suitable electric current (e.g., AC and/or DC) at any suitable frequency. For a detailed discussion of the construction and operation of exemplary electrosurgical devices and electrosurgical energy sources, reference may be made to U.S. Patent Publication Nos. 2013/0267947 and 2013/0255063; and U.S. Pat. Nos. 7,156,844 and 5,766,167, the entire contents of each of which are incorporated by reference herein.

With reference to FIGS. 1A-3, the tool assembly 100 is coupled (releasably or integrally) to a body portion 10 (FIG. 1B), e.g., a handpiece, of an electrosurgical device. For example, the body portion 10 of the electrosurgical device may include a switch 20 to control electrical communication between the electrosurgical energy source and an active lead 300 for selectively activating the active lead 300 to cut tissue. The tool assembly 100 includes a base portion 110, formed of or coated with an electrically-insulative material. The tool assembly 100 supports a return lead 210 electrically coupled to an electrosurgical energy source (e.g., via a return terminal), the active lead 300 electrically coupled to the electrosurgical energy source (e.g., via an active terminal), and an electrical insulator 400 extending distally from the base portion 110. The return lead 210 serves as an electrical return for electrosurgical energy (e.g., electric current) conducted through the active lead 300. In order to facilitate, e.g., plunge, cutting of tissue, the return lead 210 is movable relative to the active lead 300, as will be described below. In embodiments, tool assembly 100 is configured to connect to a robotic arm of a robotic surgical system to enable manipulation and control thereof.

With reference to FIGS. 1A and 2, the base portion 110 defines a central cavity (not shown) configured to receive an actuation assembly 280 of the return lead 210 as will be described below. The base portion 110 further includes a supply line 112, e.g., an electrical contact pin, electrically coupling the active lead 300 to the active terminal of the electrosurgical energy source, and a return line 114, e.g., an electrical contact pin, electrically coupling the return lead 210 to the return terminal of the electrosurgical energy source. The electrical insulator 400 extends distally from the base portion 110. In embodiments, the electrical insulator 400 may be secured with the base portion 110 by, e.g., friction fit, ultrasonic welding, etc. In embodiments, the electrical insulator 400 may be formed of a ceramic material due to its hardness and inherent ability to withstand high temperature fluctuations. Alternatively, the electrical insulator 400 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamideimide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

The electrical insulator 400 is configured to operatively support the return lead 210 and the active lead 300. In particular, the electrical insulator 400 includes a substantially flat profile and a distal edge 402 supporting the active lead 300 thereon. The active lead 300 may be formed of, e.g., tungsten. The active lead 300 may cover the distal edge 402. The active lead 300 may be configured to provide, e.g., a line, contact with tissue to minimize the surface contacting tissue. The distal edge 402 may define, e.g., an acute angle, with respect to a longitudinal axis "L-L" defined by the tool assembly 100, to facilitate cutting of tissue by the active lead 300. The distal edge 402 may be linear, may define a curvature, or may include different segments of linear and/or curved portions connected to one another to define distal edge 402. In addition, the electrical insulator 400 defines a slot 402 extending along a length of the electrical insulator 400. The slot 402 is configured to receive a camming pin 302 slidably received therein, as will be described below.

The return lead 210 includes a neck portion 210a axially extending along the longitudinal axis "L-L" of the tool assembly 100, and an engaging portion 210b extending distally from the neck portion 210a and offset from the longitudinal axis "L-L" such that the engaging portion 210b defines, e.g., an acute angle, with respect to the longitudinal axis "L-L." In embodiments, the engaging portion 210b may be spaced apart from and parallel to the distal edge 402. In addition, a portion of the engaging portion 210b may extend laterally outwards from a lateral wall 400a of the electrical insulator 400. In embodiments, the neck portion 210a and the engaging portion 210b may be formed as a single construct. In other embodiments, the neck portion 210a and the engaging portion 210b may be monolithically formed of stainless steel. The engaging portion 210b may be linear, may define a curvature, or may include different segments of linear and/or curved portions connected to one another to define engaging portion 210b. Any portion of the return lead 210 may serve as an electrical return for electrosurgical energy (e.g., electric current) conducted through the active lead 300. A large surface area of the return lead 210 compared to the small surface area of the active lead 300 may provide a desirable ratio of return surface area to cutting surface area for high efficiency in cutting tissue.

With reference to FIGS. 1A-3, in order to facilitate, e.g., plunge, cutting of tissue, the return lead 210 is movable relative to the active lead 300. In particular, the return lead 210 is configured to rotate about the camming pin 302 (FIG. 2) slidably received in the slot 402 defined in the electrical insulator 400. The return lead 210 is also configured for axial displacement along the longitudinal axis "L-L" (FIG. 3). To this end, the actuation assembly 280 is utilized to effect the rotation and axial translation of the return lead 210. The actuation assembly 280 includes an axial member 282 coupled to the camming pin 302, a torsion spring 284, and a compression spring 132. The torsion spring 284 is coupled to the neck portion 210a of the return lead 210 and the axial member 282. The engaging portion 210b is rotatable between a first orientation, in which, the engaging portion 210b is parallel to the distal edge 402 and/or defines an acute angle with respect to the longitudinal axis "L-L," and a second orientation, in which, the engaging portion 210b is rotated about the camming pin 382 in a direction of an arrow "C" (FIG. 2). The engaging portion 210b is biased towards the first orientation via the torsion spring 284. The camming pin 302 is slidably received in the slot 402 of the electrical insulator 400 through a bore 284a (FIGS. 4A and 4B) of the torsion spring 284 such that the return lead 210 and the axial member 282 are movable as a single construct. Under such a configuration, the axial member 282 along with the active lead 210 are transitionable between a proximal position and a distal position. In addition, the compression spring 132 is coupled to an anchor 130 of the base portion 110 and the axial member 282 such that the axial member 282 is biased towards the distal position. Under such a configuration, when the engaging portion 210b of the return lead 210 engages tissue, the engaging portion 210b may be pushed proximally and/or rotated in the direction of the arrow "C," i.e., away from the distal edge 402 supporting the active lead 300, to facilitate, e.g., plunge, cutting of tissue.

The return lead 210 may contact tissue at approximately the same time as the active lead 300, and thus allowing it to cut tissue. The return lead 210 returns the electrosurgical energy to the electrosurgical energy source. In this manner, the electrosurgical energy applied via the active lead 300 across tissue severs tissue in contact with the active lead 300.

In use, a clinician may position the tool assembly 100 operatively coupled to an electrosurgical device adjacent a target tissue. When the active lead 300 engages tissue to be cut, the return lead 210 may be pushed against the surrounding tissue. When the active lead 300 is further pushed into tissue, the engaging portion 210b of the return lead 210 is rotated about the camming pin 382 and/or axially displaced away from the distal edge 402 of the electrical insulator 400, which, in turn, exposes the active lead 300 engaging tissue. Under such a configuration, the rotation and axial displacement of the engaging portion 210b of the return lead 210 facilitate cutting of tissue by the active lead 300. Further, with tissue urging the engaging portion 210b proximally and/or to rotate in the direction of the arrow "C," the biasing forces applied by the compression spring 132 and the torsion spring 284 bias the engaging portion 210b into contact with the tissue to help ensure sufficient contact to facilitate tissue cutting. In order to cut tissue from a surgical site, the electrosurgical device is activated by actuating the switch 20 of the body portion 10 (see FIG. 1B) to supply electrosurgical energy to the active lead 300. Activation of the electrosurgical device draws the electrosurgical energy from the electrosurgical energy source to the active lead 300. For example, the engaging portion 210b of the return lead 210 is configured to contact tissue at approximately the same time as the active lead 300, and thus performing a cut in tissue. However, any portion of the return lead 210 may serve as an electrical return for electrosurgical energy (e.g., electric current) conducted through the active lead 300. The return lead 210 returns the electrosurgical energy to the electrosurgical energy source via the return terminal of the electrosurgical energy source. Under such a configuration, the electrosurgical energy applied via the active lead 300 across tissue severs the tissue. This process may be repeated as necessary. After tissue is removed, the clinician may coagulate and/or cauterize the tissue to control bleeding, if necessary.

Figure 6:
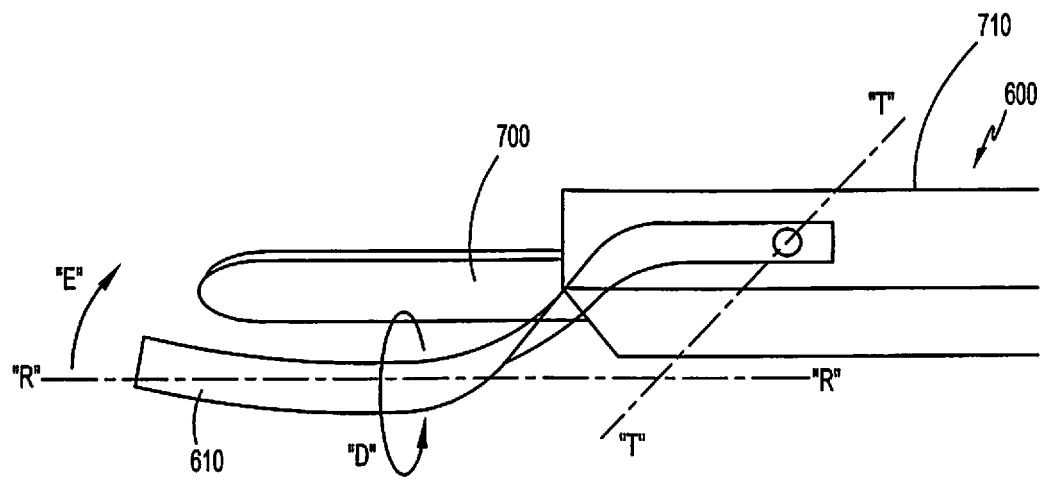
FIG. 6 is a side cross-sectional view of a tool assembly for use with an electrosurgical device in accordance with yet another aspect of the present disclosure.

While the return lead 210 is shown to be pivotable about the camming pin 382 and axially movable along the longitudinal axis "L-L," it is also envisioned that a tool assembly 600 (FIG. 6) may include a return lead 610 that is rotatable about two axes. For example, the return lead 610 is rotatable about an axis "T-T" to enable rotation of the return lead 610 in a direction of an arrow "E" and rotatable about a longitudinal axis "R-R" defined by the return lead 610 to enable rotation of the return lead 610 in a direction of an arrow "D". Under such a configuration, the return lead 610 may be rotatable in the direction of arrow "E" and the direction of arrow "D", while the return lead 610 is axially stationary with respect to the base portion 710. In this manner, the return lead 610 may be displaced away from the active lead 700 to facilitate cutting of tissue by the active lead 700.

Figure 7:
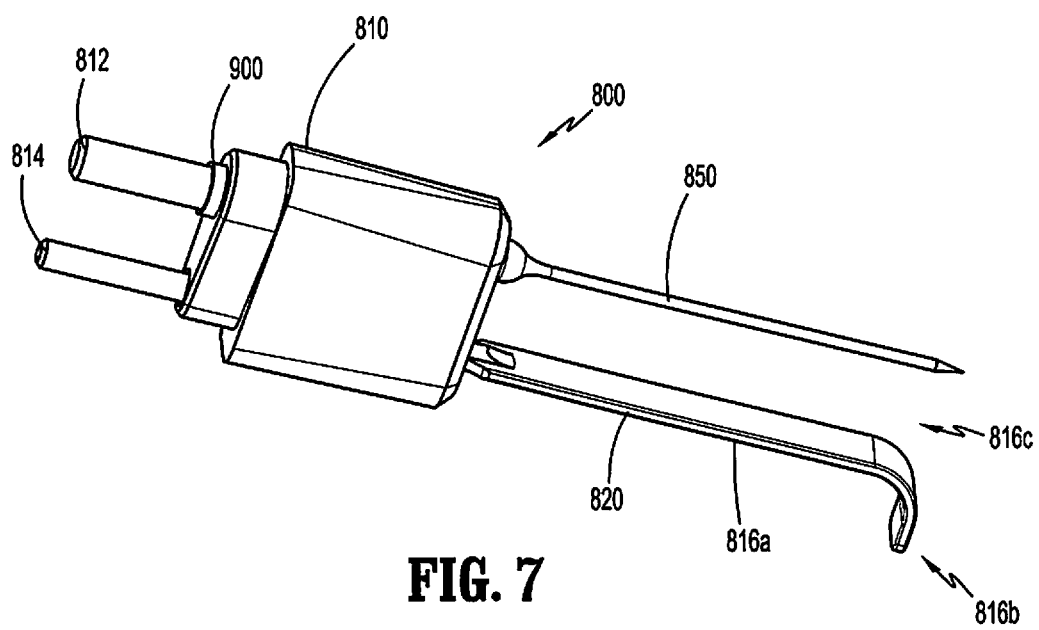
FIG. 7 is a perspective view of a tool assembly for use with an electrosurgical device in accordance with still yet another aspect of the present disclosure.

With reference now to FIG. 7, there is provided a tool assembly 800 for use with an electrosurgical device in accordance with another aspect of the present disclosure. In the interest of brevity, portions of the tool assembly 800 substantially similar to the portion of the tool assemblies 100, 700 will not be described herein to avoid obscuring the present disclosure in unnecessary detail. The tool assembly 800 is adapted to be coupled (releasably or integrally) to a body portion 10 (reference FIG. 1B), e.g., a handpiece, of an electrosurgical device to cut tissue. For example, the body portion of the electrosurgical device may include a switch to control electrical communication between the electrosurgical energy source and an active lead 850 for selectively activating the active lead 850 to cut tissue. The tool assembly 800 includes a return lead 820, a base portion 810 supporting the return lead 820 electrically coupled to the electrosurgical energy source (e.g., via a return terminal), and the active lead 850 electrically coupled to the electrosurgical energy source (e.g., via an active terminal). In contrast to the tool assembly 100, the return lead 820 and the active lead 850 of the tool assembly 800 are stationary relative to each other as will be described below.

The base portion 810 may be formed of or coated with an electrically-insulative material. The base portion 810 supports the return lead 820 electrically coupled to the electrosurgical energy source (e.g., via the return terminal), the active lead 850 electrically coupled to the electrosurgical energy source (e.g., via the active terminal), and an electrical insulator 900 extending through the base portion 810 and supporting the active lead 850 therethrough. In embodiments, the electrical insulator 900 may be secured with the base portion 110 by, e.g., friction fit, ultrasonic welding, etc. The return lead 820 serves as an electrical return for electrosurgical energy (e.g., electric current) conducted through the active lead 850. The active lead 850 may be formed of a conductive material such, e.g., tungsten. In embodiments, the return lead 820 may be formed as a single construct.

The base portion 810 defines first and second bores (not shown) configured to receive the respective return lead 820 and the active lead 850 therethrough. The electrical insulator 900 extends through the first bore of the base portion 810 and is configured to support the active lead 850 therethrough. The base portion 810 includes a supply line 812 extending proximally from the base portion 810 and electrically coupling the active lead 850 with the active terminal of the electrosurgical energy source, and a return line 814 extending proximally from the base portion 810 and electrically coupling the return lead 820 with the return terminal of the electrosurgical energy source.

In embodiments, the electrical insulator 900 may be formed of a ceramic material due to its hardness and inherent ability to withstand high temperature fluctuations. Alternatively, the electrical insulator 900 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

The active lead 850 is in a form of a needle having a sharp point, although other configurations, e.g., a blunt tip, angled tip, curved tip, etc. are also contemplated. The small surface area of the active lead 850 relative to a large surface area of the return lead 820 provides high efficiency in cutting tissue. The return lead 820 includes an extension portion 816a and an engaging portion 816b. The extension portion 816a of the return lead 820 is spaced apart from the active lead 850 thereby defining a gap 816c therebetween. In embodiments, the extension portion 816a of the return lead 820 and the active lead 850 may be parallel to each other. The engaging portion 816b of the return lead 820 is substantially orthogonal to the extension portion 816a and extends away from the active lead 850. In embodiments, the extension portion 816a and the engaging portion 816b may be monolithically formed of stainless steel. In embodiments, tool assembly 800 may be configured to connect to a robotic arm of a robotic surgical system to enable manipulation and control thereof.

In order to cut tissue from a surgical site, the electrosurgical device is activated by actuating the switch to supply electrosurgical energy to the active lead 850. Activation of the electrosurgical device draws the electrosurgical energy from the electrosurgical energy source to the active lead 850. For example, the engaging portion 816b of the return lead 820 is configured to contact tissue at approximately the same time as the active lead 850, and thus performing a cut in tissue. The return lead 820 returns the electrosurgical energy to the electrosurgical energy source via the return terminal of the electrosurgical energy source. Under such a configuration, the electrosurgical energy applied via the active lead 850 across tissue severs tissue. The small tissue-contacting surface area of the active lead 850 relative to a large tissue-contacting surface area of the return lead 820 provides high efficiency in cutting tissue. The use and operation of the tool assembly 800 are otherwise substantially similar to the use and operation of the tool assemblies described hereinabove, and thus will not be described herein.

Figure 8:
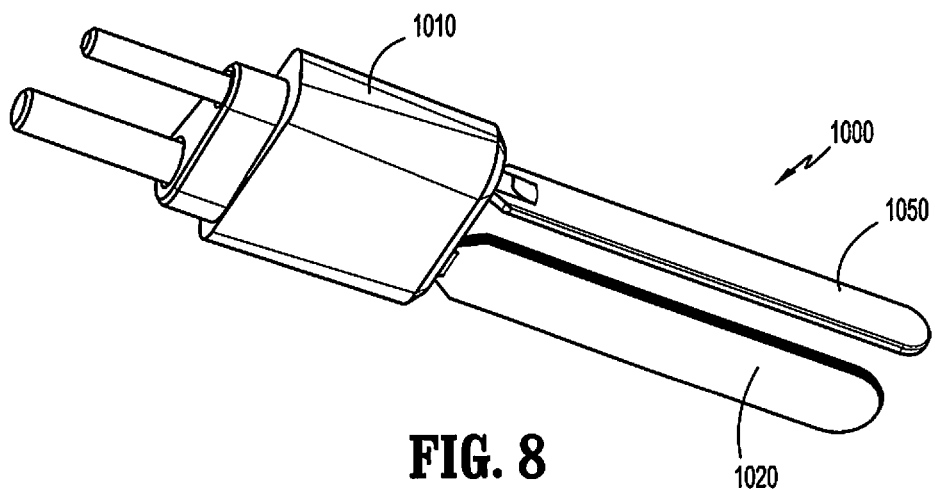
FIG. 8 is a perspective view of a tool assembly for use with an electrosurgical device in accordance with still yet another aspect of the present disclosure.

As discussed hereinabove, a small tissue-contacting surface area of an active lead relative to a large tissue-contacting surface area of a return lead provides high efficiency in cutting tissue. To this end, the active lead 850 of the tool assembly 800 is provided as a needle. However, it is further contemplated that the needle may be replaced with other configurations such as, e.g., a thin blade. With reference now to FIG. 8, a tool assembly 1000 includes an active lead 1050 extending distally from a base portion 1010 and electrically coupled to an active terminal of an electrosurgical energy source. The active lead 1050 has a thin blade configured to cut tissue. In the interest of brevity, portions of the tool assembly 1000 substantially similar to the portion of the tool assemblies 100, 800 (FIGS. 1A and 7, respectively) will not be described herein to avoid obscuring the present disclosure in unnecessary detail. The return lead 1020 is spaced apart from the active lead 1050. The base portion 1010 may be made of, e.g., polymer or other suitable insulative material. The return lead 1020 may be monolithically formed of stainless steel. Accordingly, any portion of the return lead 1020 may serve as an electrical return for electrosurgical energy (e.g., electric current) conducted through the active lead 1050. For example, the return lead 1020 may contact tissue at approximately the same time as the active lead 1050, thus allowing it to cut tissue. The return lead 1020 returns the electrosurgical energy to the electrosurgical energy source. In this manner, the electrosurgical energy applied via the active lead 1050 across tissue severs tissue in contact therewith. In particular, the return lead 1020 may include a planar profile substantially orthogonal to a planar surface defined by the active lead 1050. The small surface area of the active lead 1050 relative to the large surface area of the return lead 1020 provides high efficiency in cutting tissue. Further, the relative orientation and spacing of the active lead 1050 and the return lead 1020 further facilitates, e.g., plunge cutting, of tissue by the active lead 1050. The use and operation of the tool assembly 1000 are otherwise substantially similar to the use and operation of the tool assemblies described hereinabove, and thus will not be described herein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tool assembly for use with an electrosurgical device, the tool assembly comprising:
    a base portion;
    an electrical insulator extending distally from the base portion and defining a slot configured to receive a camming pin, the camming pin configured for movement within the slot;
    a return lead adapted to be electrically coupled to a return terminal, the return lead movably supported on the electrical insulator;
    an active lead adapted to be electrically coupled to an active terminal, the active lead fixed to the electrical insulator, wherein the return lead is rotatable about a pivot and translatable along a longitudinal axis relative to the electrical insulator and the active lead, wherein, upon activation, electrosurgical energy is transmitted from the active lead through tissue to the return lead to cut tissue in contact with the active lead; and
    a spring coupled to the camming pin and configured to bias the return lead to a first rotational position, wherein the return lead is configured to rotate to a second rotational position against the bias of the spring.

2. The tool assembly according to claim 1, wherein the active lead is fixed to a peripheral portion of the electrical insulator that defines an acute angle with the longitudinal axis.

3. The tool assembly according to claim 2, wherein the return lead includes a neck portion extending along the longitudinal axis, and an engaging portion offset from the longitudinal axis.

4. The tool assembly according to claim 3, wherein the engaging portion of the return lead is rotatable about a pivot on the neck portion of the return lead.

5. The tool assembly according to claim 4, wherein the engaging portion of the return lead is parallel to the peripheral portion of the electrical insulator when the return lead is in the first rotational position, and the engaging portion defines an acute angle with the peripheral portion of the electrical insulator when the return lead is in the second rotational position.

6. The tool assembly according to claim 1, wherein the spring is a torsion spring.

7. The tool assembly according to claim 6, wherein the camming pin extends through an opening of the torsion spring.

8. The tool assembly according to claim 1, wherein the base portion includes an axial member operatively coupled with the camming pin, and a compression spring configured to bias the axial member towards a distal-most position.

9. The tool assembly according to claim 8, wherein the compression spring is disposed along the longitudinal axis.

10. The tool assembly according to claim 1, wherein the electrical insulator is formed of ceramic.

11. The tool assembly according to claim 1, wherein the return lead is formed of stainless steel.

12. The tool assembly according to claim 1, wherein the active lead is formed of tungsten.

13. The tool assembly according to claim 1, wherein a portion of the return lead is dimensioned to be laterally outward of a lateral portion of the electrical insulator.

14. A tool assembly for use with an electrosurgical device, the tool assembly comprising:
    an electrical insulator defining a longitudinal axis;
    an active lead fixed to a distal edge of the electrical insulator;
    a camming pin received through a slot defined by the electrical insulator, the camming pin configured for axial movement within the slot along the longitudinal axis;
    a return lead coupled to the camming pin such that the return lead is configured to:
        move axially along the longitudinal axis and relative to the electrical insulator in response to corresponding axial movement of the camming pin along the longitudinal axis; and
        rotate about the camming pin relative to the electrical insulator; and
    a spring configured to bias the camming pin distally along the longitudinal axis such that proximal axial movement of the return lead is against the bias of the spring.

15. The tool assembly according to claim 14, further comprising a torsion spring defining a bore through which the camming pin is received to couple the torsion spring to the camming pin, wherein the torsion spring biases the return lead to a first rotational position relative to the electrical insulator and the return lead is configured to rotate relative to the electrical insulator against the bias of the torsion spring to a second rotational position relative to the electrical insulator.

16. The tool assembly according to claim 14, wherein the electrical insulator and the return lead are coupled to a base portion that houses the spring.

17. The tool assembly according to claim 14, wherein the return lead includes a neck portion and an engaging portion extending distally from the neck portion and along an axis offset from a longitudinal axis defined by the neck portion.

18. The tool assembly according to claim 17, wherein the return lead is configured to rotate between a first rotational position wherein the neck portion is parallel to the longitudinal axis defined by the electrical insulator and a second rotational position wherein the neck portion is transverse to the longitudinal axis defined by the electrical insulator.

19. The tool assembly according to claim 18, wherein at least a portion of the engaging portion extends parallel to the distal edge of the electrical insulator when the return lead is in the first rotational position.

20. A tool assembly for use with an electrosurgical device, the tool assembly comprising:
    an electrical insulator defining a longitudinal axis;
    an active lead fixed to a distal edge of the electrical insulator;
    a camming pin configured for axial movement within a slot defined by the electrical insulator;
    a return lead coupled to the camming pin and having a distal-most end disposed proximal to the distal edge of the electrical insulator, the return lead configured to rotate relative to the electrical insulator between a first rotational position wherein the distal end of the return lead extends laterally outward from a lateral edge of the electrical insulator a first distance and a second rotational position wherein the distal end of the return lead extends laterally outward from the lateral edge of the electrical insulator a second distance different than the first distance; and a spring coupled to the camming pin and configured to bias the return lead to the first rotational position, wherein the return lead is configured to rotate to the second rotational position against the bias of the spring.

* * * * *